US00PP14788P2

(12) United States Plant Patent
Vandenberg

(10) Patent No.: US PP14,788 P2
(45) Date of Patent: May 18, 2004

(54) CHRYSANTHEMUM PLANT NAMED 'TREAT'

(50) Latin Name: *Chrysanthemum×morifolium*
Varietal Denomination: Treat

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/452,065

(22) Filed: Jun. 2, 2003

(51) Int. Cl.[7] ..... A01H 5/00
(52) U.S. Cl. ..... Plt./289
(58) Field of Search ..... Plt./289, 287

*Primary Examiner*—Bruce R. Campell
*Assistant Examiner*—June Hwu
(74) *Attorney, Agent, or Firm*—C. A. Whealy

(57) ABSTRACT

A distinct cultivar of Chrysanthemum plant named 'Treat', characterized by its upright plant habit; large decorative spider-type inflorescences that are about 17 cm in diameter; attractive bright yellow-colored ray florets; response time about 53 days; dark green-colored foliage; strong and thick flowering stems; and excellent postproduction longevity with inflorescences and foliage maintaining good substance and color for about 21 days in an interior environment.

1 Drawing Sheet

Botanical classification/cultivar designation: *Chrysanthemum×morifolium* cultivar Treat.

BACKGROUND OF THE INVENTION

The present invention relates to a new and distinct cultivar of Chrysanthemum plant, botanically known as *Chrysanthemum×morifolium* and hereinafter referred to by the name 'Treat'.

The new Chrysanthemum is a product of a planned breeding program conducted by the Inventor in Salinas, Calif. and Alva, Fla. The objective of the breeding program is to create new cut Chrysanthemum cultivars having inflorescences with desirable colors and good form and substance.

The new Chrysanthemum originated from a cross-pollination made by the Inventor in October, 1998, in Salinas, Calif., of a proprietary *Chrysanthemum×morifolium* seedling selection identified as code number R089, not patented, as the female, or seed, parent with a proprietary *Chrysanthemum×morifolium* seedling selection identified as R210, not patented, as the male, or pollen, parent.

The cultivar Treat was discovered and selected by the Inventor as a flowering plant within the progeny of the stated cross-pollination in a controlled environment in Alva, Fla., in November, 1999. The selection of this plant was based on its desirable inflorescence color and good form and substance.

Asexual reproduction of the new Chrysanthemum by terminal cuttings taken in a controlled environment in Alva, Fla. since February, 2000, has shown that the unique features of this new Chrysanthemum are stable and reproduced true to type in successive generations.

SUMMARY OF THE INVENTION

Plants of the cultivar Treat have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Treat'.

These characteristics in combination distinguish 'Treat' as a new and distinct cultivar:

1. Upright cut Chrysanthemum that is usually grown as a disbud.
2. Large decorative spider-type inflorescences that are about 17 cm in diameter.
4. Attractive bright yellow-colored ray florets.
5. Response time about 53 days.
6. Dark green foliage.
7. Strong and thick flowering stems.
8. Excellent postproduction longevity with inflorescences and foliage maintaining good substance and color for about 21 days in an interior environment.

Plants of the new Chrysanthemum can be compared to plants of the female parent selection. In side-by-side comparisons conducted in Alva, Fla., plants of the new Chrysanthemum differed from plants of the female parent selection in the following characteristics:

1. Plants of the new Chrysanthemum had taller flowering stems than plants of the female parent selection.
2. Plants of the new Chrysanthemum had larger inflorescences than plants of the female parent selection.

Plants of the new Chrysanthemum can be compared to plants of the male parent selection. In side-by-side comparisons conducted in Alva, Fla., plants of the new Chrysanthemum differed primarily from plants of the male parent selection in the following characteristics:

1. Plants of the new Chrysanthemum produced very few disc florets and no pollen whereas plants of the male parent selection produce many disc florets with pollen.
2. Ray florets of plants of the new Chrysanthemum and the male parent selection differed in coloration as ray florets of the male parent selection were white in color.

Plants of the new Chrysanthemum can also be compared to plants of the *Chrysanthemum×morifolium* cultivar Super Yellow, not patented. In side-by-side comparisons conducted in Alva, Fla., plants of the new Chrysanthemum differed from plants of the cultivar Super Yellow in the following characteristics:

1. Plants of the new Chrysanthemum had taller flowering stems than plants of the cultivar Super Yellow.
2. Plants of the new Chrysanthemum flowered about ten days earlier than plants of the cultivar Super Yellow.
3. Plants of the new Chrysanthemum had larger and more uniform inflorescences than plants of the cultivar Super Yellow.
4. Ray floret color of plants of the new Chrysanthemum was darker yellow than ray floret color of plants of the cultivar Super Yellow.

BRIEF DESCRIPTION OF THE PHOTOGRAPH

The accompanying colored photograph illustrates the overall appearance of the new Chrysanthemum, showing the colors as true as it is reasonably possible to obtain in colored reproductions of this type. Colors in the photograph may differ slightly from the color values cited in the detailed botanical description which accurately describe the colors of the new Chrysanthemum. The photograph comprises a side perspective view of a typical flowering stem of 'Treat' grown as a disbud.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in La Ceja, Antioquia, Colombia, South America, under conditions which approximate commercial practice in a single-layer polyethylene-covered greenhouse. Two-week old rooted cuttings were planted on Aug. 19, 2002 and received 14 long day/short nights followed by short day/long nights until flowering. Plants were grown as disbudded cut Chrysanthemums. During the production time, the following environmental conditions were measured: day temperatures, 20 to 27° C.; night temperatures, 8 to 13° C.; and light levels, 4,000 to 6,000 foot-candles. Measurements and numerical values represent averages for six to ten typical flowering stems and were taken about ten weeks after the start of short days.

Botanical classification: *Chrysanthemum×morifolium* cultivar Treat.

Commercial classification: Decorative spider-type cut Chrysanthemum.

Parentage:

*Female or seed parent.*—Proprietary *Chrysanthemum× morifolium* seedling selection identified as code number R089, not patented.

*Male or pollen parent.*—Proprietary *Chrysanthemum× morifolium* seedling selection identified as code number R210, not patented.

Propagation:

*Type.*—Terminal tip cuttings.

*Time to rooting.*—About 10 to 14 days with soil temperatures of 18 to 21° C.

*Root description.*—Fine, fibrous and well-branched.

Plant description:

*Appearance.*—Herbaceous decorative spider-type cut flower that is typically grown as a disbud.

*Flowering stem (peduncle) description.*—Aspect: Erect. Length: About 127 cm. Diameter (inflorescence): About 17 cm. Diameter (base of flowering stem): About 5.25 mm. Internode length: About 4.75 cm. Texture: Pubescent; longitudinally ridged. Color: 146A.

*Foliage description.*—Arrangement: Alternate. Length: About 10.8 cm. Width: About 7.1 cm. Apex: Mucronate to cuspidate. Base: Attenuate. Margin: Palmately lobed; sinuses divergent. Texture: Upper and lower surfaces pubescent; smooth and leathery; veins prominent on lower surface. Color: Developing foliage, upper surface: Darker green than 147A. Developing foliage, lower surface: Darker green than 147B. Fully expanded foliage, upper surface: Much darker green than 147A. Fully expanded foliage, lower surface: Darker green than 147B. Venation, upper and lower surfaces: Close to 146A. Petiole: Length: About 1.7 cm. Diameter: About 3 mm. Color, upper and lower surfaces: Close to 146B.

Flowering description:

*Appearance.*—Decorative spider-type inflorescence form with quilled-shaped ray florets. Inflorescences borne on terminals, arising from leaf axils. Disc and ray florets develop acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 53 days later when grown as a disbud.

*Postproduction longevity.*—In an interior environment, inflorescences and foliage will maintain good color and substance for about 21 days in an interior environment.

*Quantity of inflorescences.*—Grown as a disbud, one inflorescence per flowering stem.

*Inflorescence size.*—Diameter: Large, about 17 cm. Depth (height): About 5.7 cm. Diameter of disc: About 2.5 mm. Diameter of receptacle: About 1 cm.

*Inflorescence buds.*—Shape: Oblate. Height: About 8 mm. Diameter: About 1 cm. Color: Darker green than 147A.

*Ray florets.*—Shape: Tubular, quilled. Length: About 8.6 cm. Width: About 5 mm. Corolla tube length: About 8.3 cm. Apex: Emarginate. Base: Fused. Texture: Smooth, velvety, glabrous; longitudinally ridged. Aspect: Initially upright; when mature, mostly perpendicular to peduncle; with development, mid-section and base, curved downward; apex, curved upward. Number of ray florets per inflorescence: About 320 arranged in numerous rows. Color: When opening and fully opened, upper surface: 6A. When opening and fully opened, lower surface: 6A.

*Disc florets.*—Shape: Tubular, elongated. Length: About 6.5 mm. Width: Apex: About 1.5 mm. Base: About 1 mm. Number of disc florets per inflorescence: Few, typically fewer than ten. Color: Immature: Close to 144A. Mature: Apex: 9A. Mid-section: Close to 145B to 145C. Base: Close to 155D.

*Phyllaries.*—Quantity per inflorescence: About 35. Length: About 1.2 cm. Width: About 3.5 mm. Shape: Lanceolate to deltoid. Apex: Acute. Base: Truncate. Margin: Entire. Texture, upper surface: Smooth, waxy. Texture, lower surface: Pubescent. Color, upper surface: Close to 146A. Color, lower surface: Darker green than 147A.

*Reproductive organs.*—Androecium: Present on disc florets only. Anther color: 9A. Amount of pollen: None observed. Gynoecium: Present on both ray and disc florets.

*Seed/fruit.*—Seed and fruit production has not been observed.

Disease/pest resistance: Resistance to pathogens and pests common to Chrysanthemums has not been observed on plants grown under commercial conditions.

Temperature tolerance: Plants of the new Chrysanthemum have demonstrated good tolerance to low temperatures of 5° C. and high temperatures high temperatures of 35° C.

It is claimed:

1. A new and distinct cultivar of Chrysanthemum plant named 'Treat', as illustrated and described.

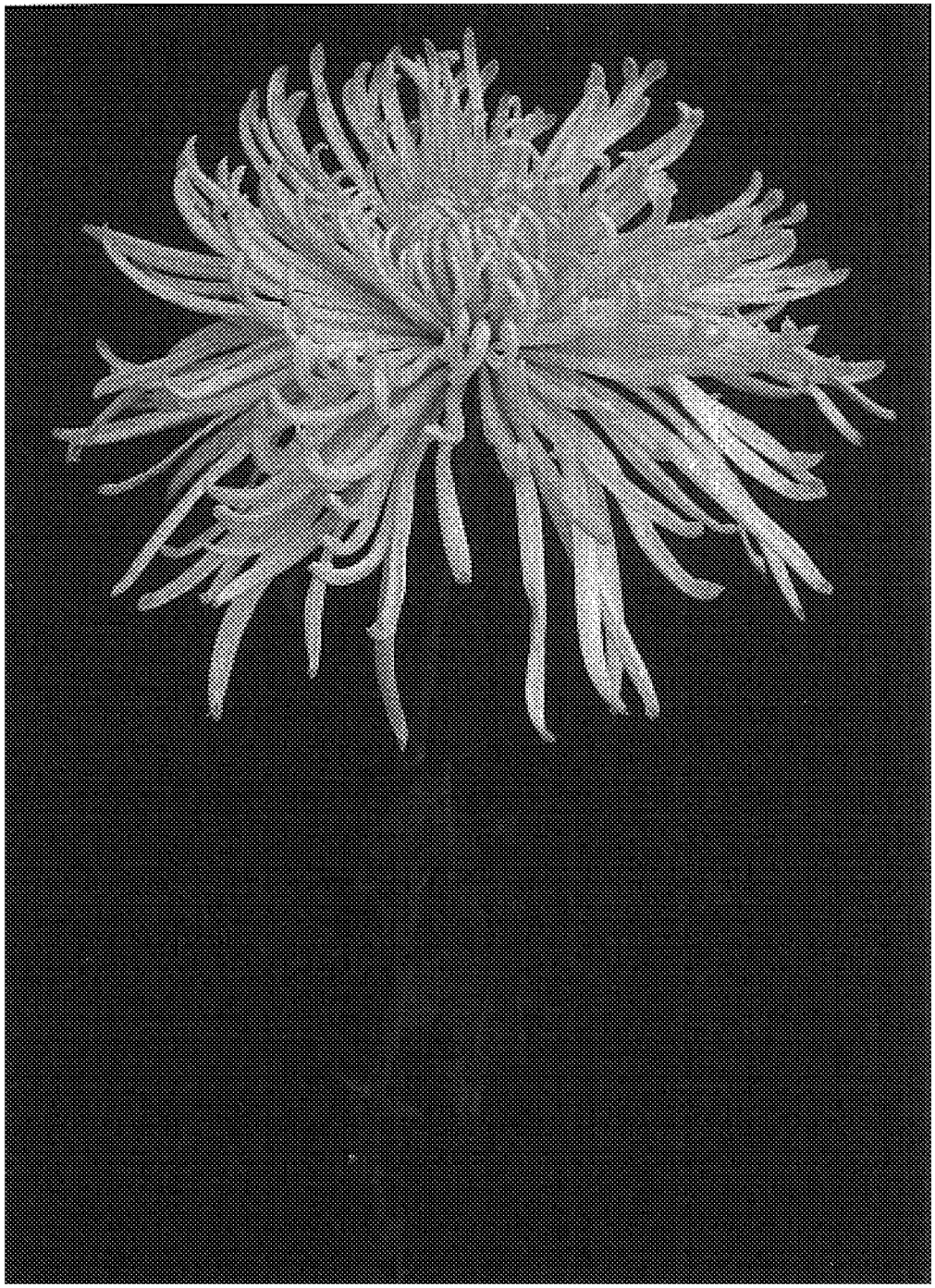

* * * * *